United States Patent [19]

Green et al.

[11] Patent Number: 5,355,913
[45] Date of Patent: Oct. 18, 1994

[54] SURGICAL REPAIR DEVICE

[75] Inventors: David T. Green, Westport; Henry Bolanos, East Norwalk; Thomas W. Alesi, Jr., New Fairfield, all of Conn.; Kenneth E. Toso, Portchester, N.Y.

[73] Assignee: United States Surgical Corporation, Norwalk, Conn.

[21] Appl. No.: 959,273

[22] Filed: Oct. 9, 1992

[51] Int. Cl.$^5$ .............................................. B21F 9/02
[52] U.S. Cl. ................................ 140/123.6; 140/93.4
[58] Field of Search .................... 140/93.2, 93.4, 123.5, 140/123.6

[56] References Cited

U.S. PATENT DOCUMENTS

| | | |
|---|---|---|
| 1,717,766 | 6/1929 | Eimler . |
| 1,950,799 | 3/1934 | Jones . |
| 2,146,104 | 2/1939 | Adamson . |
| 2,622,292 | 12/1952 | Pehaczek . |
| 2,948,939 | 8/1960 | Prete, Jr. . |
| 2,987,062 | 6/1961 | Ellison . |
| 3,111,945 | 11/1963 | Von Solbrig . |
| 3,469,573 | 9/1969 | Florio . |
| 3,473,528 | 10/1969 | Mishkin et al. . |
| 3,570,497 | 3/1971 | Lemole . |
| 3,577,601 | 5/1971 | Mariani . |
| 3,802,438 | 4/1974 | Wolvek . |
| 3,931,838 | 1/1976 | Bakermans . |
| 4,037,603 | 7/1977 | Wendorff . |
| 4,056,128 | 11/1977 | Konrad .............................. 140/93.4 |
| 4,069,554 | 1/1978 | Minolla et al. . |
| 4,119,091 | 10/1978 | Partridge . |
| 4,136,422 | 1/1979 | Ivanov et al. . |
| 4,201,215 | 5/1980 | Crossett et al. . |
| 4,202,384 | 5/1980 | Aubert . |
| 4,208,770 | 6/1980 | Takada . |
| 4,252,158 | 2/1981 | McDade . |
| 4,263,904 | 4/1981 | Judet . |
| 4,279,248 | 7/1981 | Gabbay . |
| 4,371,192 | 2/1983 | Alix . |
| 4,386,452 | 6/1983 | Stephenson . |
| 4,387,489 | 6/1983 | Dudek . |
| 4,390,047 | 6/1983 | Kaneko . |
| 4,512,346 | 4/1985 | Lemole . |
| 4,535,764 | 8/1985 | Ebert . |
| 4,542,883 | 9/1985 | Rutzki . |
| 4,551,889 | 11/1985 | Narayan et al. . |
| 4,561,475 | 12/1985 | Hinden . |
| 4,574,848 | 3/1986 | Bartzick et al. . |
| 4,583,541 | 4/1986 | Barry . |

(List continued on next page.)

FOREIGN PATENT DOCUMENTS

| | | |
|---|---|---|
| 2730571 | 1/1978 | Fed. Rep. of Germany . |
| 3042699 | 5/1981 | Fed. Rep. of Germany . |
| 3244680 | 6/1984 | Fed. Rep. of Germany . |
| 9210460 | 8/1992 | France . |

*Primary Examiner*—Lowell A. Larson

[57] ABSTRACT

A surgical apparatus for tightening a strap loop to a predetermined tension about split tissue portions includes a frame, an advancing mechanism for tightening the strap loop, a linkage mechanism which severs excess strap material not used in securing the tissue portions together and a control mechanism for controlling operation of the apparatus. The advancing mechanism includes a tensioning lever and a gear mechanism. The gear mechanism includes a tensioning hub and a clutch which releases when the tension in the strap loop exceeds a predetermined value. The control mechanism includes a safety feature for preventing inadvertent activation of the linkage mechanism. A buckle and a method for use with the surgical apparatus is also disclosed. The invention is particularly contemplated for repair of the human sternum when the sternum has been split during surgical procedures.

33 Claims, 10 Drawing Sheets

U.S. PATENT DOCUMENTS

| | | |
|---|---|---|
| 4,608,735 | 9/1986 | Kasai . |
| 4,625,717 | 12/1986 | Covitz . |
| 4,643,178 | 2/1987 | Nastari et al. . |
| 4,667,662 | 5/1987 | Titone et al. . |
| 4,730,615 | 3/1988 | Sutherland et al. . |
| 4,754,530 | 7/1988 | Lindblad . |
| 4,791,709 | 12/1988 | Fildan . |
| 4,792,336 | 12/1988 | Hlavacek et al. . |
| 4,802,477 | 2/1989 | Gabbay . |
| 4,804,383 | 2/1989 | Rey et al. . |
| 4,813,416 | 3/1989 | Pollak et al. . |
| 4,826,250 | 5/1989 | Ibanez . |
| 4,878,271 | 11/1989 | Kitokovsky . |
| 4,896,668 | 1/1990 | Popoff et al. . |
| 4,920,959 | 5/1990 | Witzel et al. . |
| 4,928,738 | 5/1990 | Marelin et al. ................... 140/123.6 |
| 4,943,292 | 7/1990 | Foux . |
| 4,944,753 | 7/1990 | Burgess et al. . |
| 4,947,901 | 8/1990 | Rancour et al. . |
| 4,955,913 | 9/1990 | Robinson . |
| 4,966,600 | 10/1990 | Songer et al. . |
| 5,023,980 | 6/1991 | Thomas . |
| 5,024,618 | 6/1991 | Tepic . |
| 5,029,433 | 7/1991 | Werk . |
| 5,048,575 | 9/1991 | Smith . |
| 5,058,365 | 10/1991 | Kägi . |
| 5,123,153 | 6/1992 | Krauss . |
| 5,139,498 | 8/1992 | Ley . |
| 5,163,598 | 11/1992 | Peters et al. . |
| 5,193,592 | 3/1993 | Evilsizer et al. ................. 140/123.6 |

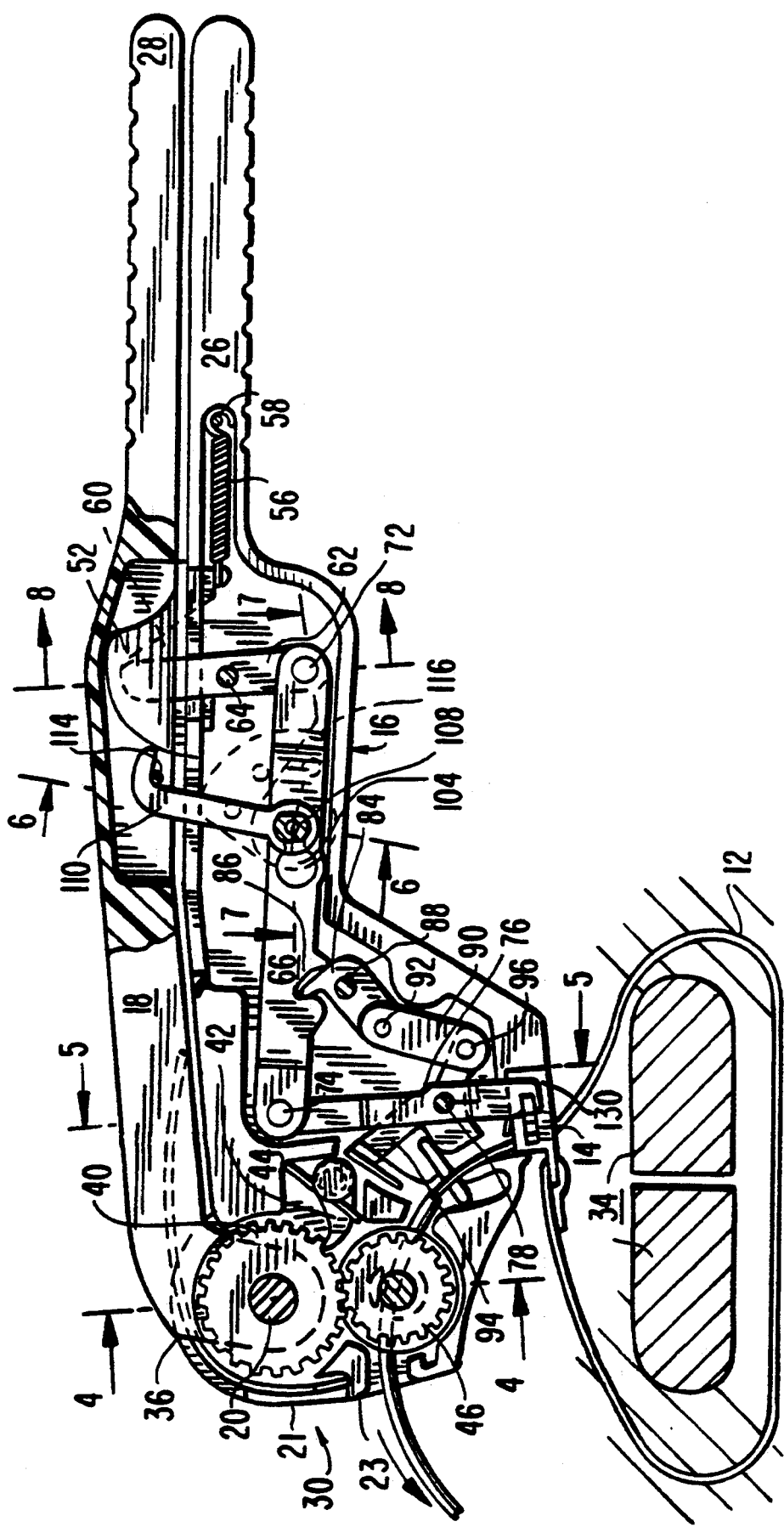

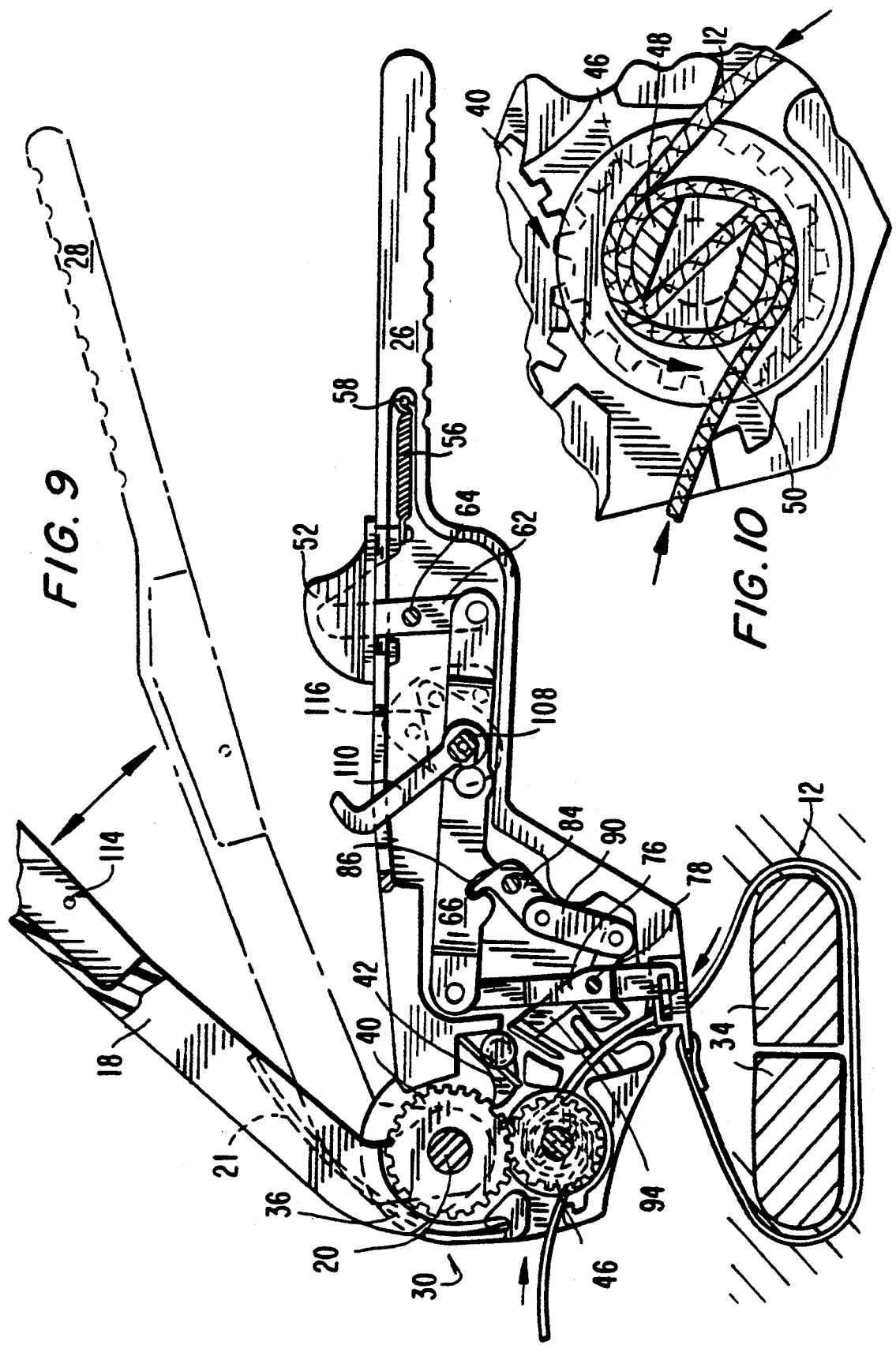

SURGICAL REPAIR DEVICE

BACKGROUND OF THE INVENTION

1. Field of the Invention

The present invention relates to a surgical device for repair of split portions of tissue. In particular, the invention is directed to a tensioning apparatus for tensioning a flexible strap to a predetermined tension about split portions of a sternum to maintain the portions in an adjacent compressive relationship during healing.

2. Description of the Prior Art

During surgery that involves a median sternotomy, e.g., open heart surgery, the sternum is split longitudinally to allow access to the organs within the thoracic cavity upon completion of the surgery, the sternum is rejoined and closed securely. For proper healing to occur, the split sternum portions must be engaged in face-to-face relationship and compressed together while the sternum heals.

Traditional methods for closing a sternum involve securing steel wires around or through the sternum halves and manually approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 to Pollak et al. which relates to a strap assembly having a curved surgical needle, an attached thin flat stainless steel strap and a buckle member. The sternum halves are brought to abutting closure by looping the strap in position around or through the sternum portions, tightening the strap to compress the sternum portions together and securing the strap within the buckle member.

A significant objective in applying the aforedescribed conventional wire and strap assemblies is to tighten the strap to an appropriate tension so as to ensure a compressed relationship between the split sternum portions during healing. However, with the methods known heretofore for applying these devices, the amount of force administered to the strap is controlled by the surgeon by discontinuing the tightening action after a determination that the sternum portions appear to be in a desired compressed relationship. Such reliance on the surgeon's ability often leads to inconsistency in the tensional force on the strap, which may result in either overtightening or insufficient tightening of the strap about the split sternum portions. A strap which is tightened excessively about the sternum portions will slice through undesired areas of tissue or bone thus presenting a potential source of infection. On the other hand, a strap which is too loose about the sternum may prolong healing.

The particular configurations of the aforementioned wire and strap assemblies also have their own shortcomings. The use of steel wires presents problems to the surgeon during the operation and to the patient after closure is completed. Steel wires are difficult to maneuver and place around the sternum. The wire edges are often sharp and can easily pierce through undesired areas including tissue surrounding the sternum area or the surgeons gloves or fingers. Further, the wire represents a non-absorbable foreign body which remains embedded within the body tissue and thus may present further complications to the patient as a result of its presence within the body.

The strap assemblies known heretofore incorporate locking mechanisms which are inherently structurally complex. For example, the locking mechanism described in U.S. Pat. No. 4,813,416 to Pollak et al. includes a buckle member having a hinge or loop segment and a spring-biased projection which projects through a loop formed in the band to maintain the closed band loop in a locked configuration. Further, the buckle assemblies are relatively small and difficult to hold against the sternum, especially during tightening of the strap through the buckle.

It would accordingly be desirable to provide a tensioning apparatus which can tighten a wire or strap about split portions of tissue, i.e., sternum portions, to a suitable desirable tension to promote uniform healing of the tissue portions while avoiding complications associated with manual tightening. It would also be desirable to provide a buckle assembly for use with the tensioning apparatus, which is simple in construction and effectively secures the strap at the desired tension about the tissue portions. Preferably, the apparatus would house the buckle assembly thereby facilitating maneuvering and control of the buckle assembly around the operative area.

SUMMARY OF THE INVENTION

Generally stated, the present invention is directed to an apparatus for tightening a strap loop about split portions of tissue to draw the tissues portions together in a contacting relation to promote healing. The apparatus comprises frame means and strap advancing means mounted in the frame means for advancing a first end portion of the strap loop in a strap tightening direction. Preferably, the strap advancing means is adapted to release and prevent further tightening of the strap loop when the tension in the strap loop exceeds a predetermined value.

The strap advancing means comprises a tensioning hub, a tensioning lever pivotally mounted to a forward portion of the frame means and gear means for transforming pivotal motion of the tensioning lever into rotational movement of the tensioning hub.

The preferred gear means comprises first gear means securely mounted about a first gear shaft, second gear means securely mounted to the tensioning hub and cooperatively engaging with the first gear means such that rotational movement of the first gear means causes reverse rotational movement of the second gear means and the tensioning hub, and clutch means securely mounted within a forward housing portion of the tensioning lever and rotatably mounted about the first gear shaft. The clutch means is adapted to engage the first gear shaft and cause rotation thereof and reverse rotation of the tensioning hub upon pivotal motion of the tensioning lever in a first direction, and to release the first gear shaft upon pivotal motion of the tensioning lever in a second direction. The clutch means preferably releases the first gear shaft when the tension in the strap loop exceeds the predetermined value.

The apparatus may also comprise linkage means for severing an excess portion of the strap loop not used in securing the split tissue portions. The linkage means comprises a vertical link member pivotally mounted in generally the center thereof to the frame means about a first stationary shaft, a driving link member longitudinally movable in response to pivotal movement of the vertical link member and having a keyway disposed in generally the center thereof, which keyway is defined by first and second apertures interconnected by a channel, a mounting link member extending generally transverse to the driving link member and pivotally movable in response to longitudinal movement of the driving link member, a pawl link member engagable with a notch formed in the driving link member and pivotable about a third stationary shaft in response to longitudinal movement of the driving link member, an intermediate link member mounted to a first end portion of the pawl link member and movable in a generally transverse direction in response to pivotal movement of the pawl link member and a knife link member having a cutting edge at a first end thereof and pivotally movable in response to transverse movement of said intermediate link member. An actuating button slidably mounted to the upper surface of the frame means and engageable with the vertical link member is moved to activate the linkage means.

In a preferred embodiment, the apparatus also comprises control means for controlling operation of the apparatus. The control means is operable within first, second and third positions. The first position corresponds to a secured position of the apparatus. The second position corresponds to an unlocked position to permit actuation of the strap advancing means and the third position corresponds to a release position which permits actuation of the linkage means. The control means is adapted to permit actuation of the linkage means only when the control means is in its third position.

The components of the control means include an eccentric shaft rotatably mounted to the frame means and received within the keyway in the drive link member. The eccentric shaft is adapted to rotate between a first, a second and a third position. Preferably, the eccentric shaft has a cross section defining a major axis and a minor axis, with the major axis being greater in length than the length of the minor axis and also being greater than the width of the channel of the keyway in the driving link member.

The control means further includes at least one locking hook member mounted to the eccentric shaft, a locking bar mounted within the tensioning lever and correspondingly positioned to be engaged by the locking hook member and at least one control lever mounted to the eccentric shaft on the exterior of the frame means.

The first position of the eccentric shaft corresponds to the first position of the control means wherein the eccentric shaft is received within the first aperture of the driving link member and has its major axis generally transverse to the longitudinal axis defined by the frame means and wherein the locking hook member engages the locking bar to secure the tensioning lever to the frame means.

The second position of the eccentric shaft corresponds to the second position of the control means wherein the locking hook member is released from its engagement with the locking bar to permit pivotal movement of the tensioning lever and tightening of the strap loop. In this position, the eccentric shaft is received within the first aperture of the driving link member and has its major axis angularly displaced relative to the longitudinal axis defined by the frame means such that the eccentric shaft engages portions of the driving link member defining the channel to prevent longitudinal movement of the driving link member and actuation of the linkage means.

The third position of the eccentric shaft corresponds to the third position of the controls means wherein the major axis of the eccentric shaft is generally parallel to the longitudinal axis defined by the frame means such that the eccentric shaft clears the channel of the keyway in the driving link member to permit longitudinal movement of the driving link member relative to the frame means and actuation of the linkage means.

The apparatus may also comprise means for securing the strap loop in the tensioned condition about the tissue portions. In a preferred embodiment, the securing means comprises buckle means. The buckle means may be releasably mounted to the frame means, preferably, to the linkage means.

The present invention is also directed to a buckle assembly for securing a strap member about split portions of tissue. The buckle assembly comprises a base member having an opening extending therethrough for reception of a portion of the strap member and means for engaging the strap member to securely retain the strap member in a compressive closed looped configuration about the split tissue portions. The base member includes a partial longitudinal channel defined between an upper and lower surface thereof.

The preferred strap member engaging means comprises clip means mounted to the base member. The clip means is pivotal from an open position which permits reception of the strap member and a closed position which securely wedges the strap member between a forward edge of the clip means and the base member. In a preferred embodiment, the clip means includes a resilient tail portion which biases the clip means to the closed position when the clip means is stressed to the open position during reception of the strap.

The strap member engaging means may further comprise clamp means slidably housed within the partial longitudinal channel of the base member and movable therewithin from a non-engaging position to an engaging position. The clamp means is adapted to securely wedge the strap member between a forward edge of the clamp means and the base member when in the engaging position. The clamp means is maintained in the engaging position by partial tab members extending from a rear portion of the base member and into the partial longitudinal channel. The partial tab members are biased slightly downwardly toward the lower surface of the base member and are adapted to engage a rear portion of the clamp means when the clamp means is advanced to the engaging position. The partial tab members are correspondingly configured and dimensioned to securely retain the clamp means in the engaging position.

The present invention is also directed to a system for tensioning a strap loop to a predetermined tension about split tissue portions. The system comprises frame means adapted to support two end portions of the strap to form a loop about the split tissue portions, means for advancing the strap in a strap tightening direction, buckle means for securing the strap loop in the tensioned condition, linkage means for severing excess portion of the strap loop not used in securing the split tissue portions and control means for controlling operation of the apparatus.

A method is also disclosed for repairing split portions of tissue. The method comprises the steps of providing an apparatus for tensioning a strap loop about split portions of tissue, the strap having a buckle member attached thereto for securing the strap in the tensioned condition, the apparatus comprising frame means and means mounted in the frame means for advancing a first end portion of the strap loop in a strap tensioning direction, looping the strap around the tissue portions, activating the strap advancing means to tighten the looped strap about the split tissue portions so that they are in an adjacent engaged relation and securing the strap member within the buckle member.

A method is also provided for securing first and second portions of a sternum with a strap having a buckle member attached to a first end portion thereof. The method comprises the steps of providing a tensioning apparatus including frame means, means mounted in the frame means for advancing a second end portion of the strap in a strap tightening direction, which strap advancing means releases and prevents further tightening of the strap when the tension in the strap exceeds a predetermined tension, linkage means for severing excess strap material not used in securing the tissue portions and control means for controlling operation of the apparatus. Preferably, the control means is operable within a first, a second and a third position. The first position corresponds to a secured position of the apparatus. The second position corresponds to an unlocked position to permit actuation of the strap advancing means and the third position corresponds to a release position to permit actuation of the linkage means. The method further comprises the steps of looping the strap around the tissue portions, advancing the control means to its second position to permit actuation of the strap advancing means, activating the strap advancing means to tighten the looped strap about the split tissue portions to the predetermined tension, advancing the control means to its third position to release the linkage means and actuating the linkage means to sever excess strap material not used in securing the tissue portions together and securing the strap member within the buckle.

BRIEF DESCRIPTION OF THE DRAWINGS

Preferred embodiments of the invention are described hereinbelow with reference to the drawings wherein:

FIG. 3 is a view partially in cross-section, taken along lines 3—3 of FIG. 1 illustrating the secured position of the apparatus;

FIG. 9 is a view similar to the view of FIG. 3 illustrating the unlocked position of the apparatus to permit ratcheting movement of the tensioning lever and tightening of the strap about the tissue portions;

FIG. 10 is a cross-sectional view of the gear mechanism illustrating coiling of the strap around the tensioning hub;

DETAILED DESCRIPTION OF THE INVENTION

Figure 1:
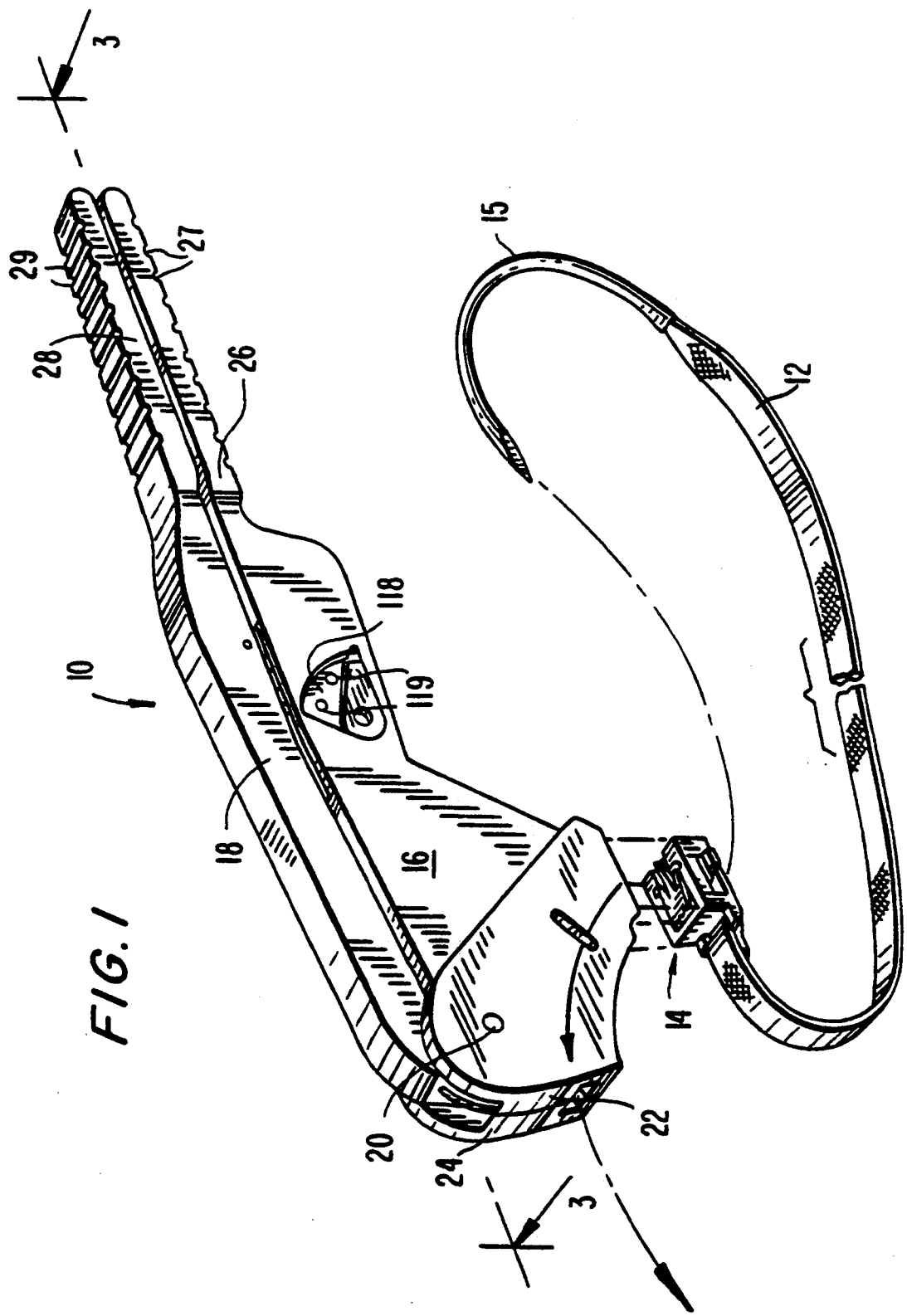
FIG. 1 is a perspective view of the apparatus for tightening a strap to a predetermined tension about split tissue portions constructed according to the present invention.

Referring initially to FIG. 1, there is illustrated a perspective view of the tensioning apparatus 10 constructed according to the present invention. Apparatus 10 is particularly configured to tighten a band or strap 12 to a predetermined tension about split portions of tissue so that the tissue portions are in an engaged and compressed relationship during healing. Strap 12 is secured in the tensioned condition by buckle 14 which is initially mounted within apparatus 10. Buckle 14 is specifically configured for operation with apparatus 10 and assumes a locked condition in response to activation of the apparatus.

Apparatus 10 includes frame member 16 and tensioning lever member 18 pivotally mounted to a forward portion of the frame member via shaft 20. Frame member 16 possesses two housing half sections 22, 24 which are configured and dimensioned to house the operating components of the apparatus 10. Frame member 16 also possesses elongated rearward portion 26 which corresponds to elongated rearward portion 28 of tensioning lever 18. Portions 26, 28 are adapted to be grasped by the user to actuate the apparatus. Portions 26, 28 include serrations 27, 29, respectively, to assist in gripping and maneuvering the apparatus.

Housing half sections 22, 24 may be formed of a suitable desirable plastic material such as polycarbonate, polypropylene, polyethylene or the like, or, in the alternative, of a metal such as stainless steel. The housing half sections are attached along a seam by suitable attachment techniques including screwing means, adhesive means and ultrasonic welding.

Figure 2:
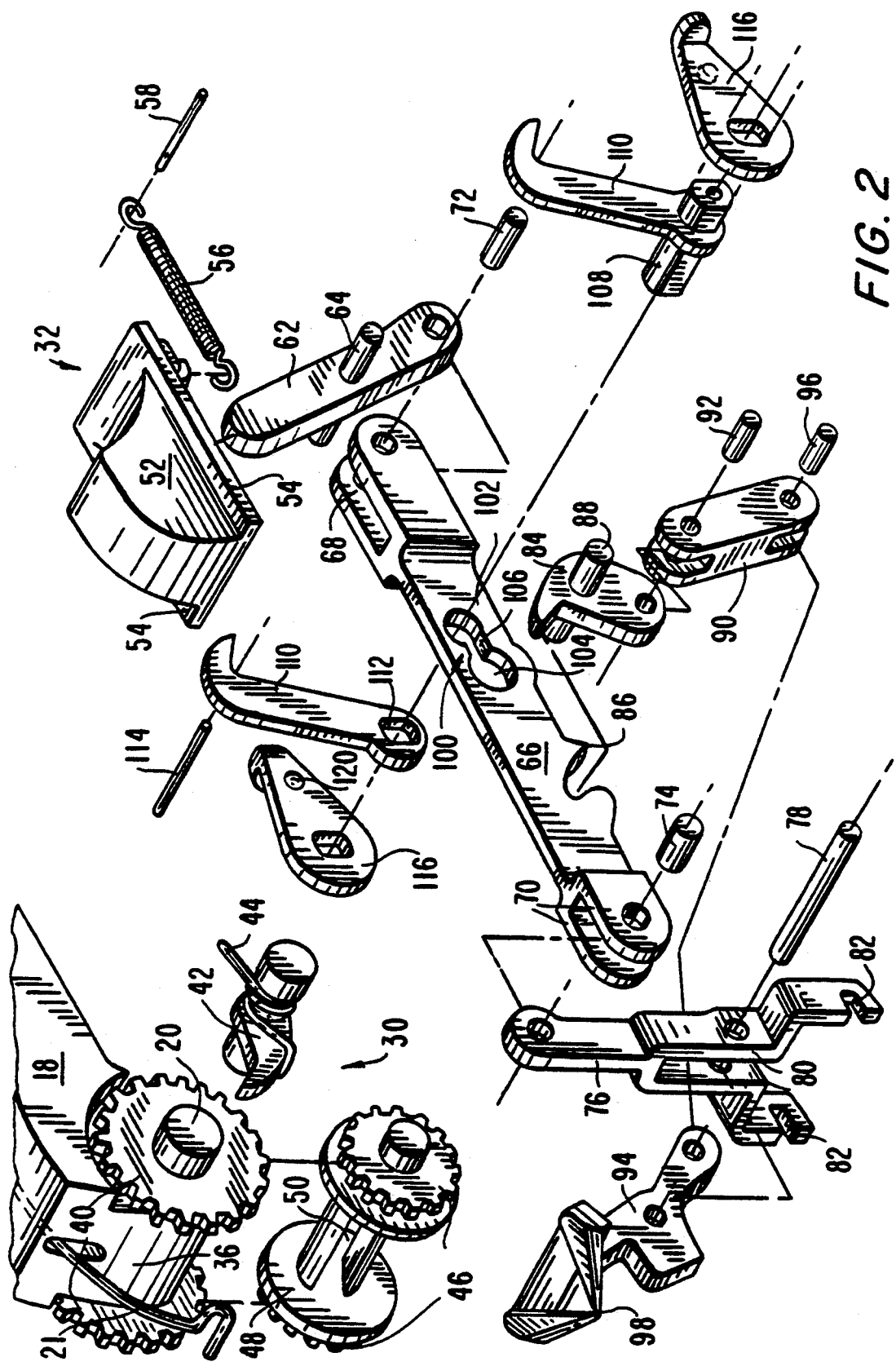
FIG. 2 is a perspective view with parts separated, of the apparatus of FIG. 1 illustrating the operative mechanism and component parts of the apparatus of FIG. 1.

Referring now to FIG. 2, apparatus 10 is shown with parts separated, so as to illustrate the novel operating mechanism of the present invention. Apparatus 10 consists essentially of two operating mechanisms: 1) a strap tensioning mechanism identified generally as numeral 30; and 2) a linkage mechanism identified generally as numeral 32. Strap tensioning mechanism 30 tightens strap 12 to a predetermined tension about the tissue portions. Linkage mechanism 32 releasably mounts buckle 14 to the applier and also severs excess strap material not utilized in securing the sternum.

Figure 4:
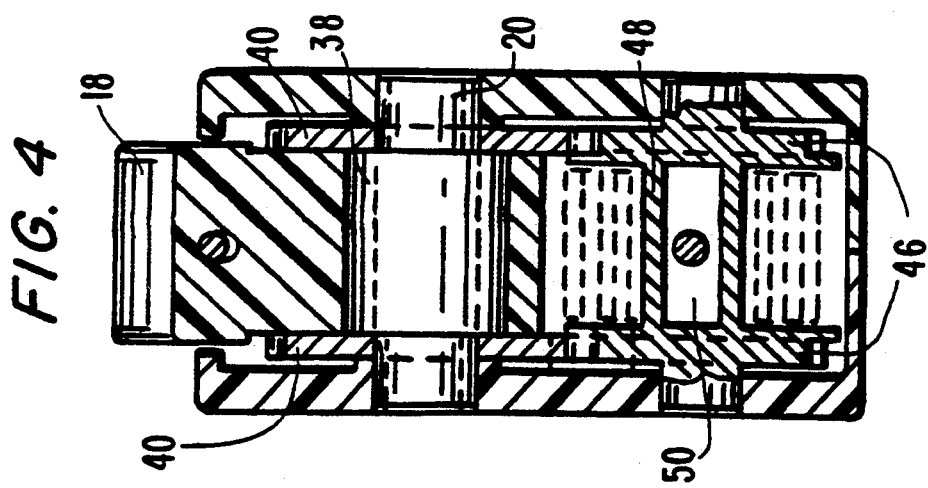
FIG. 4 is a cross-sectional view taken along lines 4—4 of FIG. 3 illustrating the cooperative engagement of the lower and upper gears of the gear mechanism.

Referring now to FIGS. 2-4, the strap tensioning mechanism 30 is illustrated in detail. Tensioning lever 18 defines a forward housing portion 36 of generally circular cross section which houses clutch mechanism 38 (FIG. 4). Preferably, clutch 38 is securely mounted to housing portion 36 and rotatably mounted about shaft 20. Clutch 38 may be of any conventional type which slips upon reaching a predetermined tension in the strap. A preferred clutch for use with the present invention is manufactured by Torrington of Connecticut and is rated to slip, due to the gearing, when the strap tension reaches approximately 25 pounds. This clutch operates in two modes: lock and overrun. In the lock mode, the relative rotation of housed clutch 38 transmits a torque to shaft 20, and, accordingly causes the shaft to rotate with the clutch. In the overrun mode, the clutch is free to overrun in one direction, thus providing a ratcheting-type action to the lever. In the preferred embodiment, clutch 38 is in the locked mode upon downward pivotal movement of tensioning lever 18 and is in the overrun mode upon upward movement of the tensioning lever.

A resilient curved lever spring 21 has a first end portion mounted within an interior channel 25 defined in tensioning lever 18 and a second end portion secured and mounted within groove 23 formed in frame 16. Spring 21 biases tensioning lever 18 to an upward or open position away from frame member 12 after each tightening or downward movement of the lever, thus placing the lever in a position for subsequent tightening action.

A pair of upper gears 40 are also mounted on shaft 20 and rotate with the shaft in response to downward (locked mode) movement of tensioning lever 18. A pawl 42 is positioned adjacent one of upper gears 40 to engage the teeth of the gear to prevent negative rotational motion of the gears after a tensioning movement of tensioning lever 18. Helical coil spring 44 is wrapped around the axis of pawl 42 to bias the pawl in a generally upward tooth engaging position.

Lower gears 46 mesh with upper gears 40 such that rotational motion of the upper gears results in reverse rotational motion of the lower gears. Lower gears 46 are securely mounted on tensioning hub 48 so that the tensioning hub rotates with the lower gears. Tensioning hub 48 has a channel 50 defined through its axis for reception of the needled end of strap 12. Rotational motion of tensioning hub 48 causes coiling of strap 12 around its axis and, consequently, tightening of the strap about the split tissue portions. (See FIG. 10)

Figure 8:
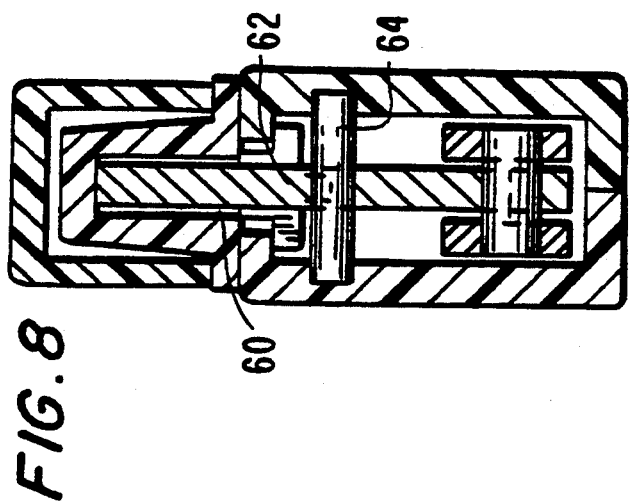
FIG. 8 is a cross-sectional view taken along lines 8—8 of FIG. 3 illustrating the actuating button and the vertical link member of the linkage mechanism.

Referring once again to FIGS. 2 and 3, linkage mechanism 32 includes actuating button 52 slidably mounted to an upper surface portion of frame member 16. Button 52 is adapted for reciprocal longitudinal movement between an unadvanced and an advanced position. Wing portions 54 extend from each side of button 52 and are received within two corresponding longitudinal grooves (not shown) formed in half sections 22, 24 to retain the button on frame member 16. A helical spring 56 is affixed to the rear end portion of button 52. Spring 56 is also attached to frame member 16 via pin 58 and biases button 52 back towards the unadvanced position. Button 52 also includes groove 60 (shown in phantom in FIG. 3) on a lower surface thereof which is configured and dimensioned to receive an upper portion of vertical link member 62. (See also FIG. 8)

Vertical link 62 extends generally transversely from button 52 and into frame member 16. Vertical link 62 pivots about stationary shaft 64 in response to longitudinal movement of button 52. Shaft 64 is disposed in generally the center of vertical link 62.

Referring further to FIGS. 2 and 3, driving link member 66 extends longitudinally within frame member 16 and is adapted for reciprocal longitudinal movement in response to the pivotal movement of vertical link 62. Driving link 66 includes two pairs of leg members 68, 70 at a rear and forward portion thereof, respectively. Leg members 68, 70 each have an aperture defined therethrough for reception of pins 72, 74 respectively. Pin 72 connects driving link 66 with vertical link 62 and pin 74 links the driving member with mounting link 76.

Figure 5:
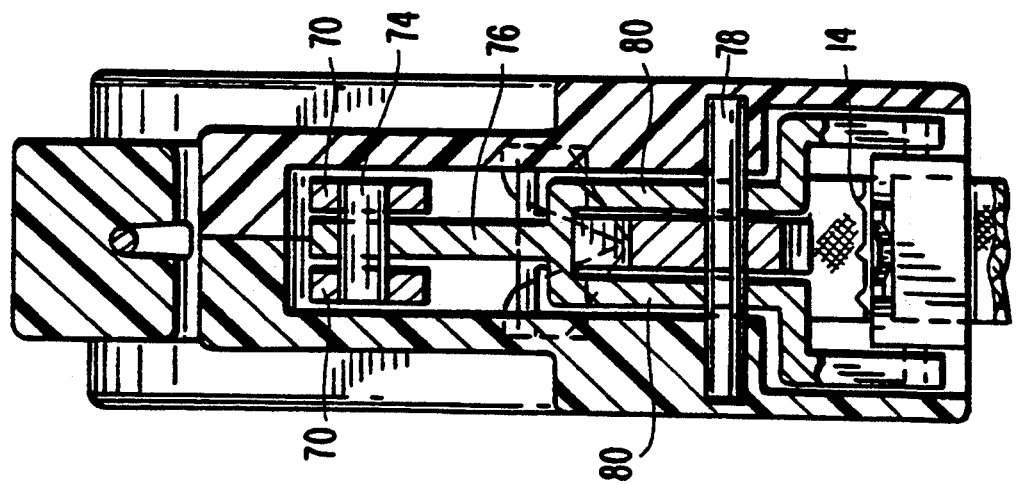
FIG. 5 is a cross-sectional view taken along lines 5—5 of FIG. 3 illustrating the mounting link member for releasably mounting the buckle to the apparatus.
Figure 12:
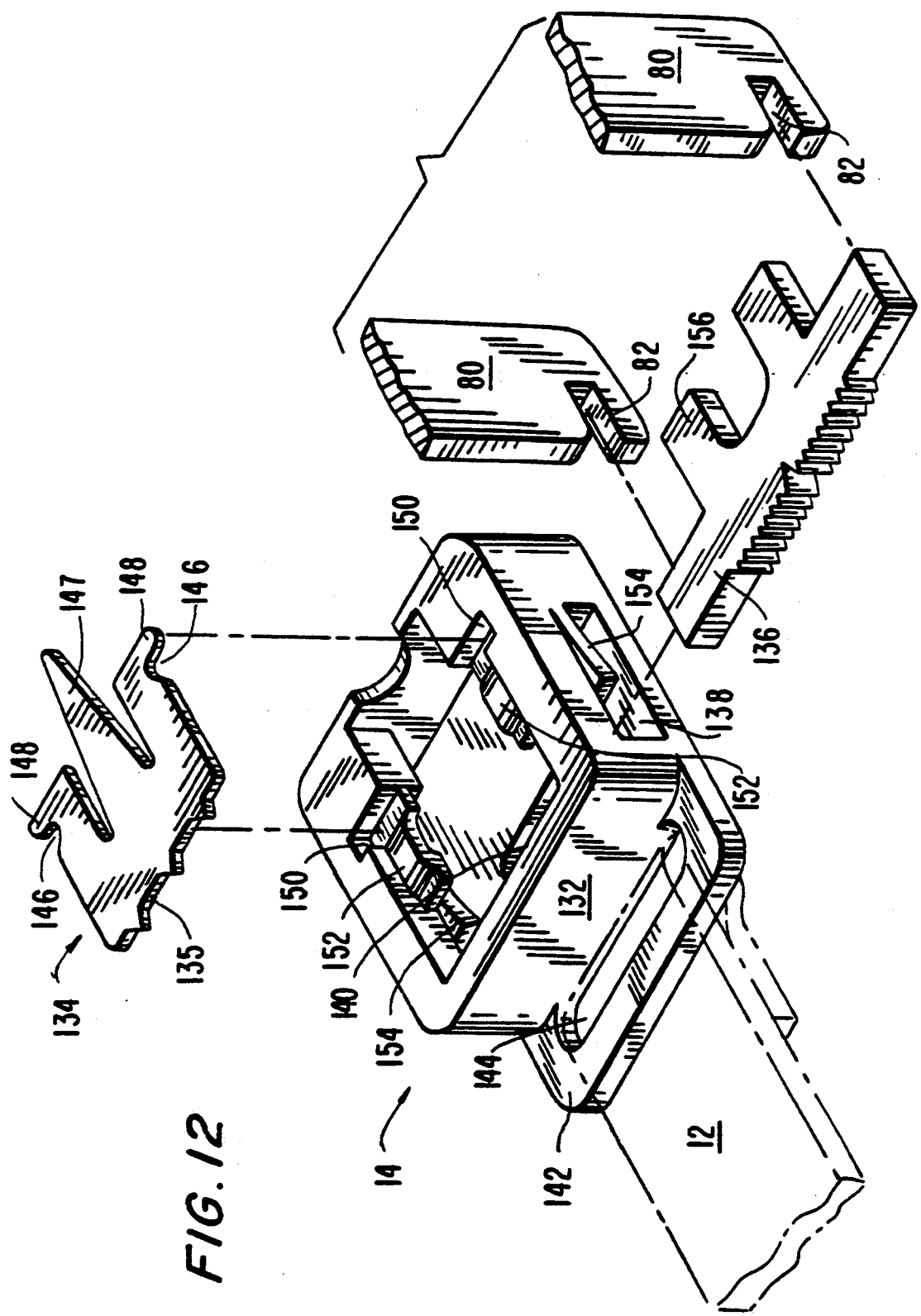
FIG. 12 is a perspective view with parts separated, of the preferred buckle assembly for use with the apparatus of FIG. 1.

Referring now to FIGS. 2 and 3, in conjunction with FIGS. 5 and 12, mounting link 76 extends generally transversely from driving link 66 and is pivotally mounted about stationary shaft 78. Mounting link 76 pivots in response to longitudinal movement of driving link 66. Mounting link 76 includes a pair of leg members 80 appropriately spaced to accommodate and mount buckle 14. Each leg member 80 has a partial longitudinal groove 82 defined in a lower portion thereof. Grooves 82 are configured to receive the clamp member 136 of buckle 14 to releasably mount the buckle to the lower surface of frame member 12. FIG. 12 illustrates this mounting in detail. Mounting link 76 also pivots to drive the clamp member of buckle 14 against the strap as will be described below.

Referring once again to FIGS. 2 and 3, pawl 84 is engagable with notch 86 formed in driving link 66 and is pivotally mounted about stationary shaft 88 and pivots in response to longitudinal movement of the driving link. Pawl 84 initiates transverse motion of intermediate link member 90.

Intermediate link 90 is connected to the lower portion of pawl 84 via pin 92 and moves in a general transverse direction relative to frame 16 in response to pivotal movement of the pawl. Intermediate link 90 is connected at its lower portion to knife link member 94 via pin 96.

Knife link 94 is received within the opening defined between leg members 80 of mounting link 76 and is pivotally mounted about stationary shaft 78. Knife 98 having a suitable cutting edge as shown is provided at the upper end portion of knife link 94 to sever excess strap material not utilized in securing the tissue portions together. Knife link 94 pivots downwardly and counterclockwise in response to transverse upward movement of intermediate link 90, causing knife 98 to cut the excess strap material.

Referring further to FIGS. 2 and 3, driving link 66 includes a keyway 100 at a position approximately intermediate the end portions of the driving link. Keyway 100 consists of two arcuate apertures 102, 104 interconnected by channel 106.

An eccentric control shaft 108 is received within keyway 100 formed in driving link 66, and is rotatable within the keyway through a rotational range of about 90°. The relative rotation of eccentric shaft 108 controls the functioning of the apparatus as will be described hereinbelow. Eccentric shaft 108 has a generally truncated circular cross-section as shown (i.e., a circular crosssection cut along two arcs by flat planes) so as to resemble a somewhat elliptical cross section which defines a major axis which is greater in dimension than its minor axis. The dimension of the minor axis is less than the width of channel 106.

Figure 6:
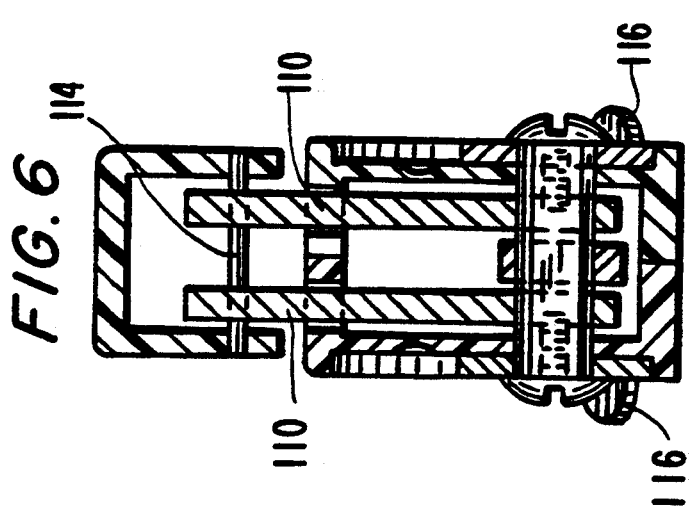
FIG. 6 is a cross-sectional view taken along lines 6—6 of FIG. 3 illustrating the locking hooks securing the tensioning lever to the frame member.

A pair of locking hooks 110 are mounted on eccentric shaft 108 and rotate along with the shaft. Locking hooks 110 possess apertures 112 which correspond in dimension to the cross section of eccentric shaft 108 to effect the mounting. In the closed or vertical position, locking hooks 110 engage locking pin 114 mounted in tensioning lever 18 to secure the lever to frame member 16. FIG. 6 illustrates this position in further detail.

Figure 7:
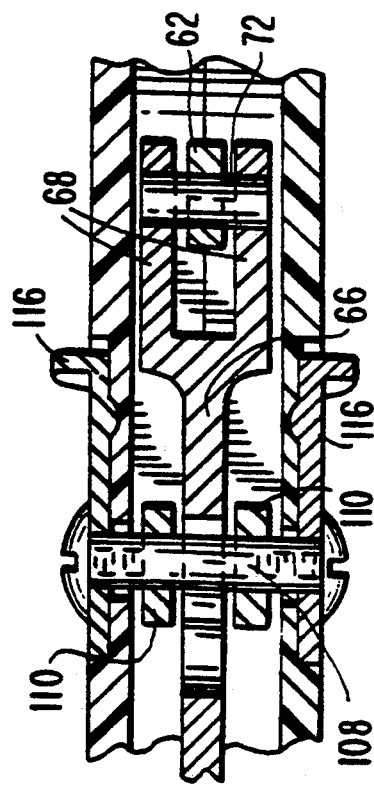
FIG. 7 is a cross-sectional view taken along lines 7—7 of FIG. 3 illustrating the control levers and the eccentric shaft of the control mechanism.

A pair of control levers 116 are also mounted on eccentric shaft 108. Control levers 116 are disposed on the exterior of frame 16 and are secured against the frame by screw means. (See also FIG. 7) Movement of control levers 116 causes rotation of eccentric shaft 108. Accordingly, levers 116 control operation of the apparatus.

Control levers 116 are movable to three positions. The first position, as shown in phantom in FIG. 3, corresponds to the locked position of apparatus 10 wherein locking hooks 110 are engaged with locking pin 114 to secure tensioning lever 18 to frame 16. In this position, the major axis of eccentric shaft 108 is generally transverse to the longitudinal axis defined by driving link 66.

Referring now to FIG. 9, the second position of control lever 116 and eccentric shaft 108 is shown in phantom. The second position corresponds to an unlocked position of tensioning lever 18 to permit ratcheting motion of the lever and thus tightening of strap 12 about tissue portions 34. In this position, locking hooks 110 are released from their engagement with locking shaft 114 and eccentric shaft 108 is rotated approximately 45° from its first position. It is to be noted that in this position of eccentric shaft 108, the shaft engages portions of driving link 66 surrounding channel 106 thereby preventing longitudinal movement of driving link 66 and thus preventing activation of the linkage mechanism.

Figure 11:
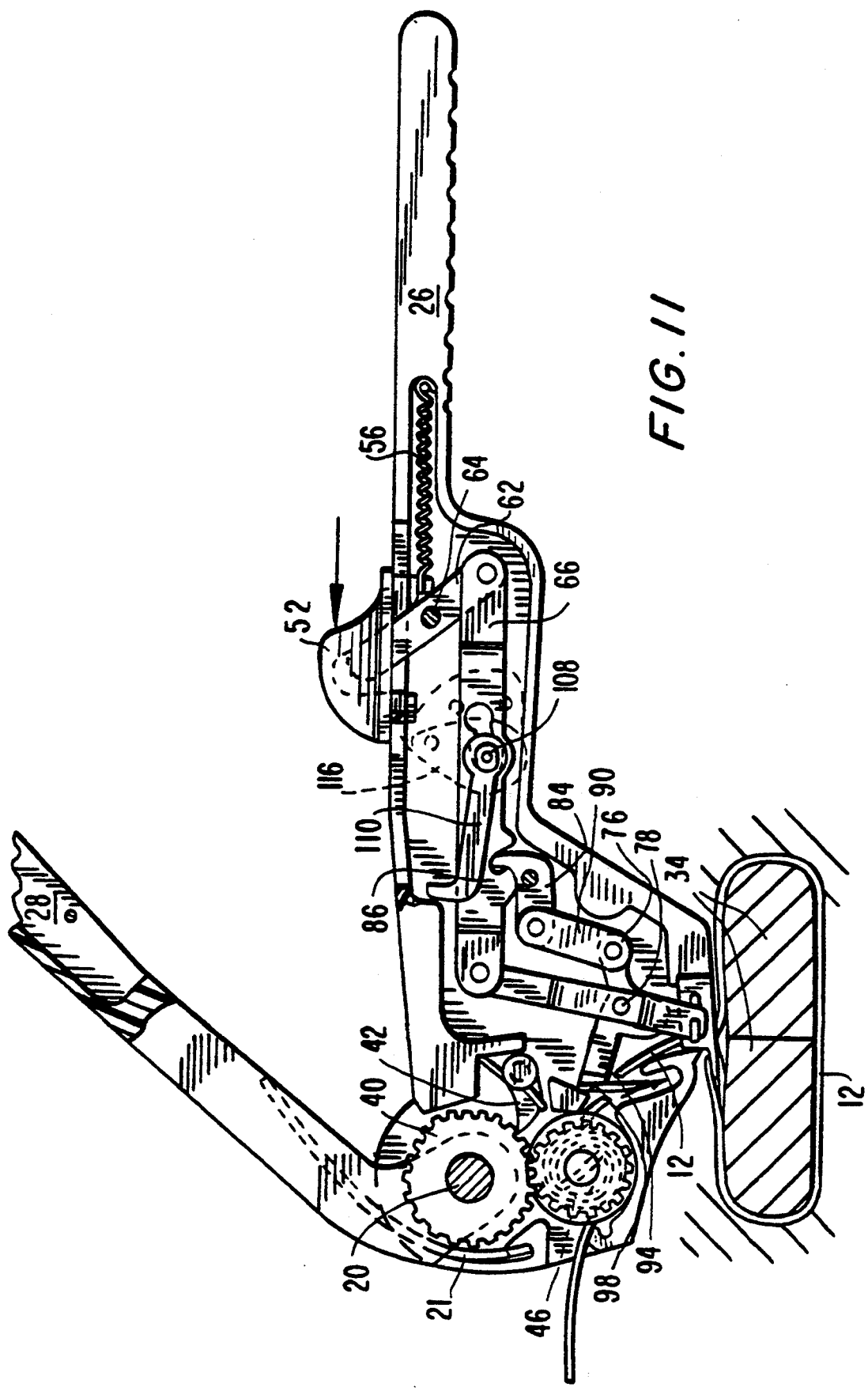
FIG. 11 is a cross-sectional view similar to the view of FIG. 3 illustrating the release position of the control mechanism to permit actuation of the linkage mechanism.

Referring now to FIG. 11, the third position of control lever 116 and eccentric shaft 108 is illustrated. In this position, eccentric shaft 108 is displaced approximately 45° relative to its second position such that the major axis of the shaft is generally parallel to the longitudinal axis defined by driving link 66. It is to be noted that in this position of eccentric shaft 108, the shaft clears channel 106 thereby permitting longitudinal movement of driving link 66. Thus, activation of the linkage mechanism is possible.

Referring again to FIG. 1, a triangular shaped recess 118 is formed on each side of frame 16 to receive and accommodate control levers 116. Each recess 118 includes three circular shaped depressions 119 which correspond to the first, second and third positions of control lever 116. A corresponding semi-spherical projection 120 (FIG. 2) extends from the surface of control lever 116 adjacent frame 16. As shown, projection 120 is correspondingly configured to be received within each of depressions 119 formed in the outer surface of frame 16. Thus, control lever 116 may be releasably locked in either of the three positions.

Referring now to FIG. 12, there is illustrated a perspective view with parts separated, of the preferred buckle assembly 14 to be used with the apparatus 10 of the present invention. Buckle assembly 14 is specifically configured to operate with apparatus 10 and includes base member 132 having clip member 134 pivotally mounted to an upper surface of the base member and a clamp member 136 slidably mounted within a partial longitudinal channel 138 defined between the upper and lower surfaces of the base member. Base member 132 has opening 140 extending therethrough for reception of the needled end of strap 12 and an extension 142 having slot 144 for securing the other end of the strap to the buckle.

Clip member 134 and clamp member 136 both secure strap 12 within buckle 14. In a preferred embodiment, clamp member 136 supplements clip member 134 in securing the strap 12. However, it is to be appreciated that both the clip member and the clamp member are configured and adapted such that each may independently securely lock and wedge strap 12 within buckle 14.

Clip member 134 may be mounted to the upper surface of base member 132 by conventional means. In a preferred embodiment, clip member 134 includes two side arcuate grooves 146 defining arcuate tabs 148 which are received within correspondingly configured and dimensioned grooves 150 formed in the upper surface of base member 132. The upper surface portion adjacent grooves 150 are then deformed by, for example, a peening operation, to displace surface material over a portion of the arcuate extension to enclose the extensions within the grooves, and, thereby mount clip member 134 to base member 132. In the alternative, the upper surface of base member may be provided with opposing recesses. Arcuate tabs 148 may snap into these recesses to mount the clip member to the base member.

Figure 15:
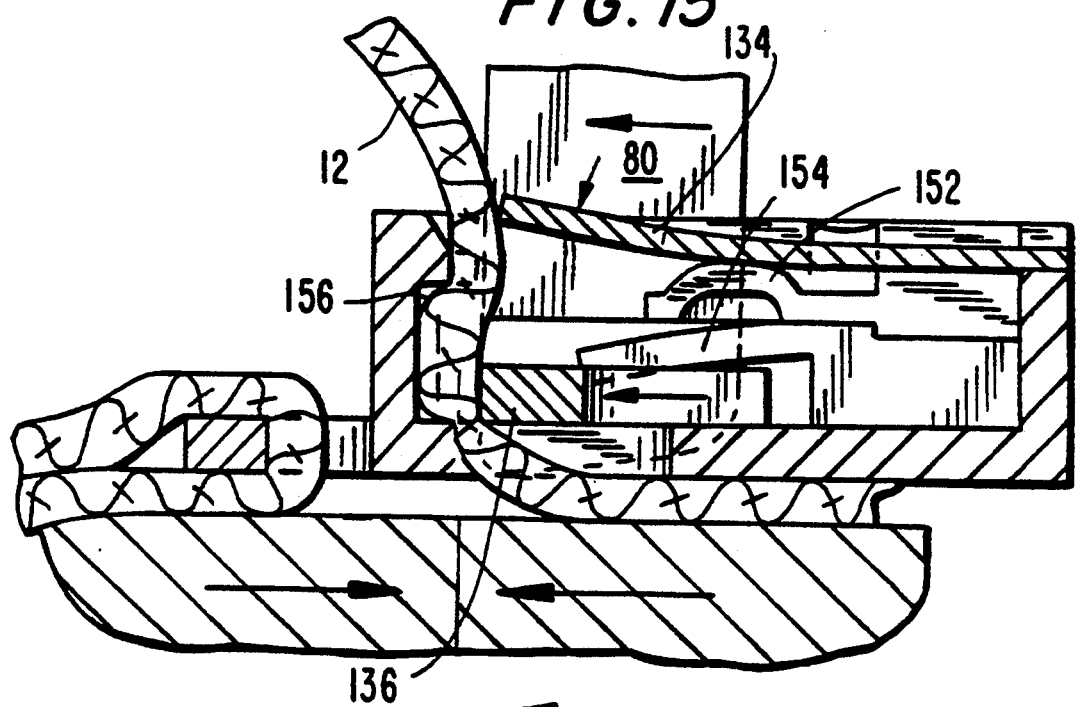
FIG. 15 is a cross-sectional view of the buckle assembly of FIG. 13 illustrating the secured position of the buckle with the clip member and the clamp member each securely engaging a portion of the strap received within the buckle.

Clip member 134 is adapted to pivot about tabs 148 from an open position (FIG. 13) to receive a portion of strap 12 to a closed position wherein forward serrated edge 135 of the clip member engages the strap (FIG. 15).

Clip member 134 is preferably fabricated from a resilient material such as stainless steel or titanium. This is a significant feature of the present invention in that the resiliency of clip member 134 provides a means to bias the clip member to the closed strap engaging position. In particular, when clip member 134 is stressed to the open strap receiving position of FIG. 13, the resiliency of the clip continuously urges forward edge 135 to its normal generally horizontal strap engaging position. Once the stress on clip member 134 is removed, i.e., the advancement of strap 12 through buckle 14 is discontinued, forward edge 135 assumes its normal position thereby wedging strap 12 against base member 132 as shown in FIG. 15. In the preferred embodiment, clip member 134 includes resilient tail portion 147 which urges forward edge 135 against base member 132 when the clip is stressed top the open position. It is to be appreciated that the resilient quality of clip member 134 and tail portion 147 is sufficient to securely wedge strap 12 against base member 132.

Referring again to FIG. 12, a pair of arcuate tabs 152 are disposed adjacent the upper surface of base member 132. Tabs 152 provide support and stability to mounted clip member 134. Tabs 152 are configured to serve as fulcrums about which clip member 134 pivots.

Clamp member 136 supplements clip member 134 in securing strap 12 within buckle 14 and about the split tissue portions. Clamp member 136 is adapted for longitudinal movement within channel 138 from an unadvanced position (FIG. 13) to an advanced strap engaging position (FIG. 15) in response to activation of linkage mechanism 32. The forward edge of clamp member 136 is preferably serrated to assist in gripping the wedged strap portion.

Figure 14:
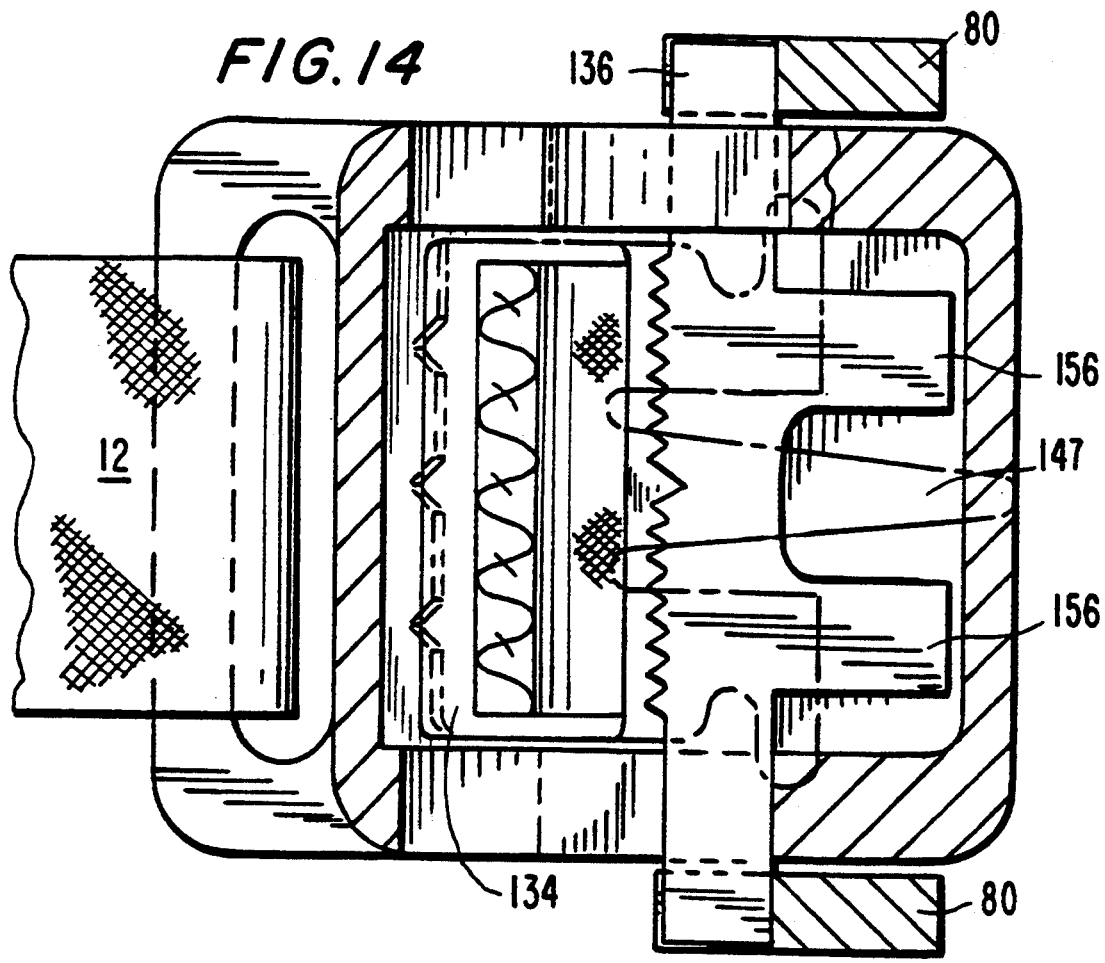
FIG. 14 is a top plan view of the buckle assembly shown in FIG. 13 further illustrating the unsecured position of the buckle.

Clamp member 136 also serves to releasably mount buckle 14 to the apparatus 10. As best shown in FIGS. 12 and 14, the side portions of clamp 136 extend beyond the sides of buckle 14 and are received within corresponding grooves 82 formed in mounting link 80 to mount the buckle to the mounting link in a suspended manner. Preferably, clamp member 136 and grooves 82 are correspondingly dimensioned to provide a capturing (loose but secure) fit between the two components.

Figure 13:
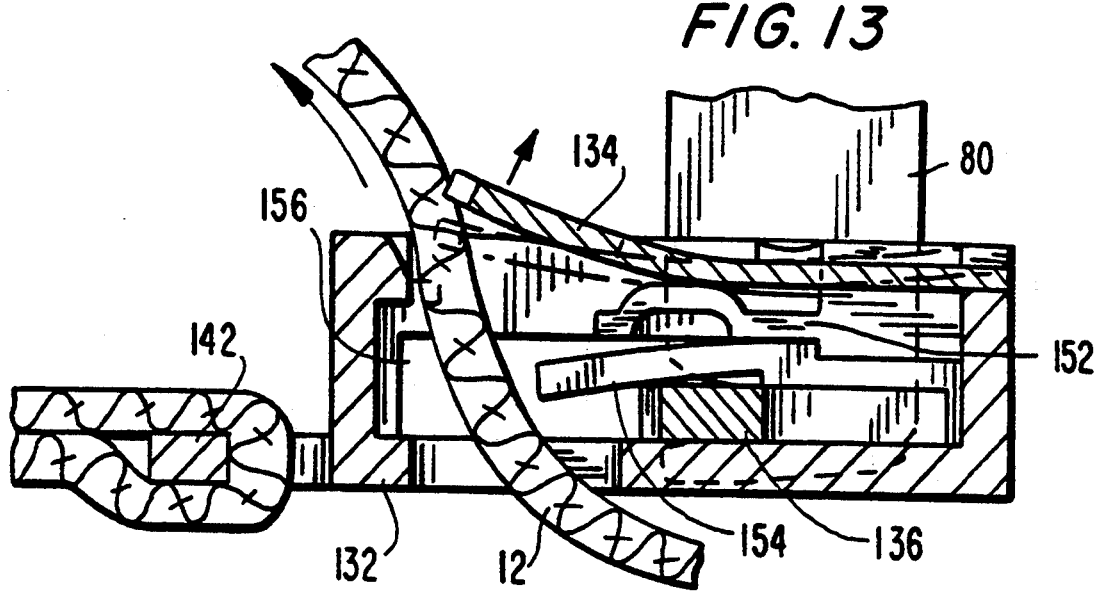
FIG. 13 is a cross-sectional view of the buckle assembly of FIG. 1 illustrating the unsecured position of the buckle.

Referring now to FIG. 12 in conjunction with FIG. 13, two downwardly biased resilient tab members 154 partially extend in the upper portion of channel 138. Downwardly biased tab members 154 are configured to engage the rear portion of clamp member 136 to retain the clamp member against strap 12 when the clamp is in the advanced strap engaging position, without damaging (weakening) the strap.

Figure 16:
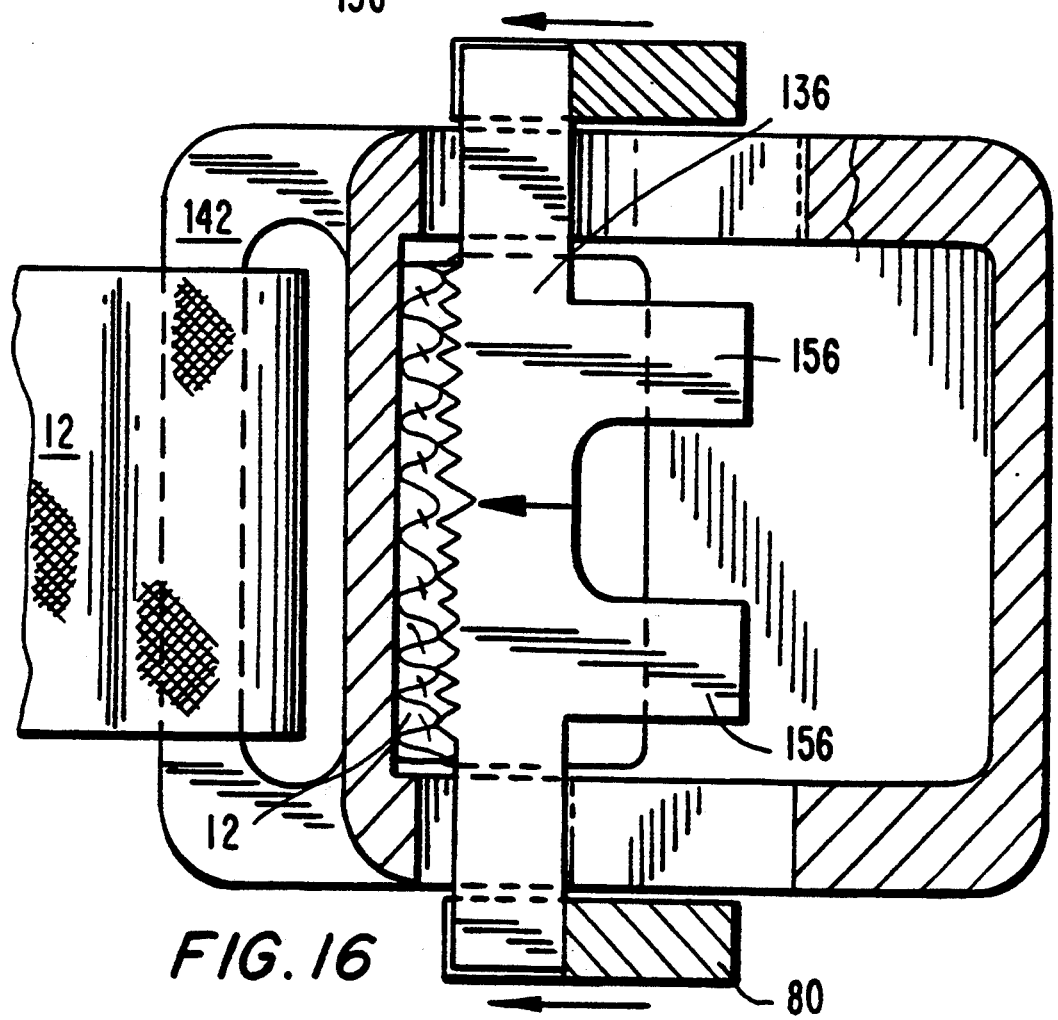
FIG. 16 is a top plan view of the buckle assembly of FIG. 15 further illustrating the secured position of the buckle.

As shown in FIG. 13, in the unadvanced condition of clamp member 136, downwardly biased tab members 154 rest on an upper surface of clamp member 136. However, once clamp member 136 is moved longitudinally to its advanced position shown in FIGS. 15 and 16, tab members 154 are released from their contact with the upper surface of the clamp member to assume their normal downwardly biased position. In this position, the forward edges of tab members 154 engage the rear edge of clamp member 136 to securely retain the clamp against strap 12. It is to be appreciated that downwardly biased tab members 154 are configured and dimensioned so as to securely retain clamp member 136 in a wedging locking engagement against the strap without damaging or weakening the strap.

As shown in FIG. 13, a pocket 156 (FIG. 13) receives the wedged portion of strap 12. Because of its cross-sectional configuration as shown, pocket 156 alters the angle in which strap 12 is received within opening 140, thus providing more surface area in which clamp member 136 can engage the strap.

Referring again to FIG. 12, clamp member 136 also includes two leg portions 156. Leg portions are engagable with tab members 154 when clamp member 136 is in the advanced strap engaging position of FIGS. 15 and 16, to thereby minimize transverse movement of the clamp member and potential release of the clamp member through the sides of buckle 14.

The components of buckle 14 are preferably fabricated from a bio-compatible metal such as stainless steel or titanium. Buckle 14 may also be fabricated from polymeric materials including acrylics, polystyrenes, polycarbonates and styrene-acrylonitrile (SAN) copolymers and formed by known injection molding techniques.

Strap 12 may be formed of any material suitable for use in stabilizing fractured bones or securing tissue portions generally. Typically, strap 12 may be fabricated from a wide variety of monofilament and braided materials both absorbable and non-absorbable, e.g., catgut, silk, nylon, polyester, polypropylene, linen, cotton and absorbable synthetic materials such as polymers and copolymers of glycolic and lactic acids. Examples of such non-absorbable materials include those fabricated from synthetic fibers such as polyesters, polyethylene, polytetrafluoroethylene and polyamides. A suitable synthetic material includes woven DACRON TM manufactured by DuPont deNemours of Wilmington, Del. In the alternative, strap 12 may be formed from a bioabsorbable material such as catgut or synthetic materials including polymers and copolymers of glycolic and lactic acids.

U.S. patent application Ser. No. 07/829,423, filed Feb. 3, 1992, the contents of which are incorporated herein by reference, discloses a strap or sternum closure ribbon which may be readily adapted for use with the buckle assembly of the present invention. The strap disclosed in this application is a braided product having a plurality of elongated filamentary reinforcing members of ultra high molecular weight polyethylene fibers. The fibers may be plasma treated to reduce slip characteristics of the yarn. The fibers exhibit strengths from about 375 kpsi (thousands of pounds per square inch) to 560 kpsi and a tensile module of from about 15 msi (millions of pounds per square inch) to about 30 msi.

Strap 12 may have a tapered end to reduce tissue trauma as well as to facilitate attachment to surgical needle 15. It is to be appreciated that strap 12 is readily pliable for forming the sternum encircling loop course.

Surgical needle 15 may be attached to a first end of strap 12 by conventional means. Needle 15 assists in penetrating the targeted parasternal location and positioning the strap under the sternum and then outwardly at an opposite parasternal location. Preferably, needle 15 is curved.

Further understanding of the apparatus 10 of the present invention will be realized from the description provided of the use of same in securing split portions of a sternum together after a sternotomy.

Referring once again to FIG. 3, apparatus 10 with mounted buckle 14 is positioned adjacent sternum portions 34. Needle 15 with attached strap 12 is inserted within a selected parasternal location at one side of the sternum and passed under both sternum portions 34 to an opposite parasternal location. Needle 15 is then pushed outwardly and exposed from the operative site, and pulled from the sternum location until a sufficient working length of strap 12 is provided. Needle 15 is inserted through opening 140 in buckle member 14 (FIG. 12), advanced through frame 16 and inserted through channel 50 of tensioning hub 48 (FIG. 2). The sternum portions are approximated and the excess slack removed by manually pulling the strap in a tightening direction.

Prior to continuing with the final tightening of strap 12, one or more tensioning apparatus with mounted buckle and strap assemblies may be placed around selected parasternal locations in the same manner. When several straps are in place around the sternum, each apparatus is ready to be tightened.

Referring now to FIG. 9, control lever 116 is advanced to its second position to release locking hook 110 from its engagement with locking bar 114 in tensioning lever 18. Tensioning lever 18 automatically pivots away from frame member 16 under the influence of leaf spring 21 (see FIG. 3) disposed in the forward portions of the lever and the frame member. Strap 12 is tightened around the split sternum portions by ratcheting motion of tensioning lever 18. Each downward motion of lever 18 towards frame member 16 effects rotational movement of upper gears 40. Rotational movement of gears 40 causes reverse rotational movement of lower gears 46 and tensioning hub 48. This rotational movement, in turn, effects coiling of strap 12 around the axis of tensioning hub 48. FIG. 10 illustrates in detail the movement of the gears (as shown by the arrows) and winding of strap 12 around tensioning hub 48.

Referring again to FIG. 9, after each ratcheting motion of lever 18, pawl 42 engages the teeth of one of gears 40 to prevent negative rotational movement of the gears and loosening of strap 12. It is to be noted that clip 134 of buckle member 14 engages the strap portion received within the buckle also to prevent loosening of strap 12.

Tightening of strap 12 around the sternum is continued until clutch 38 (FIG. 4) slips. This is a significant feature of the present invention in that the tension of strap 12 and the compressive forces of the strap on sternum portions 34 can be predetermined with the selection of a particular sized clutch 38 to ensure a compressive engaged relationship between the sternum portions during healing. This element of control helps to minimize complications associated with overtensioning of the strap, i.e. piercing or cutting of the sternum by the tightened strap, as well as complications associated with insufficient strap tensioning. Accordingly, the potential for infection or other trauma to the patient is minimized. The preferred afore-described Torrington clutch will slip when the strap tension about tensioning hub 48 reaches about 25 lbs.

Referring now to FIG. 11, control lever 116 is advanced to its third generally vertical position, which rotates eccentric shaft 108 another 45°. In this position, the major axis of eccentric shaft 108 is parallel to the axis defined by frame member 12 to thereby enable the shaft to clear interconnecting channel 106 to permit longitudinal movement of driving link 66 and activation of the linkage mechanism 32.

Actuating button 52 is then longitudinally advanced in the direction shown by the arrow to pivot vertical link 62 about stationary shaft 64. Pivoting movement of vertical link 62 exerts a rearward longitudinal force on driving link 66, which causes rearward longitudinal movement of the driving link. This movement simultaneously effects clockwise pivotal movement of pawl 84, due to its engagement with notch 86, and clockwise pivotal movement of mounting link 76 about stationary shaft 78. The pivotal movement of pawl 84 causes intermediate link 90 to move in a generally vertical direction, which lifts the rear end of knife link 94 and forces the forward cutting edge 98 of the knife downwardly to cut strap 12. It is to be appreciated that the force generated by the linkage mechanism is sufficient to completely sever strap 12.

The longitudinal movement of driving link 66 causes legs 80 of the mounting link to forcibly drive clamp member 136, which is releasably housed in grooves 82 of the legs, against the portion of strap 12 received within buckle 14. Accordingly, tabs 154 of buckle 14 are released from their engagement with the upper surface of clamp member 136 and assume their normal downwardly biased position (FIG. 15) wherein the forward edge of the tabs 154 engage the rear edge of the clamp member 136 to securely retain the clamp member against the strap portion. Actuating button 52 is released, and is returned to its unadvanced condition by spring 56. Consequently, the linkage mechanism 32 returns to its unadvanced condition of FIG. 3 with clamp member 136 being released from its mounting to mounting link 80. Accordingly, buckle 14 is released from its mounting to the apparatus.

The apparatus of the present invention effectively tightens and secures a strap to a predetermined tension about split tissue portions. The apparatus is lightweight, easy to use, and is easy to maneuver about the surgical site. It incorporates safety features to prevent inadvertent activation of the linkage mechanism. The buckle used with the apparatus provides a locking mechanism which is simple in construction and which avoids the complexities of known buckle assemblies.

Although the present invention has been described in terms of a preferred embodiment, it is to be understood that the invention is not limited to the precise embodiment, that various other changes and modifications may be effected therein by one skilled in the art without departing from the scope of the invention.

What is claimed is:

1. An apparatus for tightening a strap about split portions of tissue, which comprises:
   frame member;
   advancing means associated with said frame member for advancing a first end portion of the strap in a strap tensioning direction about split portions of tissue;
   linkage means for severing an excess portion of the strap not used in securing the split tissue portions; and
   manually operable control means for controlling operation of the apparatus said control means being operable by at least one control lever rotatably mounted to said frame member, said at least one control lever moveable between at least two positions, a first position of said at least one control lever corresponding to an actuating position to permit actuation of said advancing means a second position of said at least one control lever corresponding to a release position to permit actuation of said linkage means.

2. The apparatus according to claim 1, wherein said advancing means is adapted to release and prevent further tightening of the strap about the split tissue portions when the tension in the strap exceed a predetermined value.

3. The apparatus according to claim 2, wherein said advancing means comprises:
   a tensioning hub;
   a tensioning lever pivotally mounted to a forward portion of said frame member; and
   gear means for transforming pivotal motion of said tensioning lever into rotational movement of said tensioning hub.

4. The apparatus according to claim 3, wherein said gear means comprises:
   first gear means securely mounted about a first gear shaft;
   second gear means securely mounted to said tensioning hub and cooperatively engaging with said first gear means such that rotational movement of said first gear means causes reverse rotational movement of said second gear means and said tensioning hub; and
   clutch means securely mounted within a forward housing portion of said tensioning lever and rotatably mounted about said first gear shaft, said clutch means engaging said first gear shaft and causing rotation thereof and reverse rotation of said tensioning hub upon pivotal motion of said tensioning lever in a first direction and releasing said first gear shaft upon pivotal motion of said tensioning lever in a second direction.

5. The apparatus according to claim 4, wherein said clutch means releases said first gear shaft when the tension in the strap exceeds the predetermined value.

6. The apparatus according to claim 3, further comprising lever spring means for biasing said tensioning lever away from said frame member.

7. The apparatus according to claim 2, further comprising means for securing the strap in the tensioned condition.

8. The apparatus according to claim 1 wherein said control means is operable independent of said advancing means and said linkage means.

9. The apparatus according to claim 1 wherein said linkage means is actuated by an actuating button slidably mounted to said frame member.

10. An apparatus for tightening a strap about split portions of tissue, which comprises:
frame member;
advancing means associated with said frame member for advancing a first end portion of the strap in a strap tensioning direction about split portions of tissue;
linkage means for severing an excess portion of the strap: and
manually operable control means for controlling operation of the apparatus, said control means being operable between first, second and third positions, said first position corresponding to a secured position of the apparatus, said second position corresponding to an unlocked position to permit actuation of said strap advancing means and to prevent actuation of said linkage means and said third position corresponding to a release position to permit actuation of said linkage means.

11. The apparatus according to claim 10, wherein said linkage means comprises a plurality of interconnected link members.

12. The apparatus according to claim 9, wherein said interconnected link members include:
a vertical link member pivotally mounted in generally the center thereof to said frame member about a first stationary shaft;
a driving link member extending longitudinally relative to a longitudinal axis defined by said frame member and longitudinally movable in response to pivotal movement of said vertical link member, said driving link member having a keyway disposed in generally the center thereof, said keyway including first and second apertures connected by a channel, said driving link member connected at a first end portion thereof to said vertical link member;
a mounting link member extending generally transverse to said driving link member and pivotally mounted to said frame member about a second stationary shaft, said mounting link member connected to a second end portion of said driving link member and pivotally movable in response to longitudinal movement of said driving link member, said mounting link member defining two separated leg members;
a pawl link member engagable with a notch formed in said driving link member and pivotable about a third stationary shaft in response to longitudinal movement of said driving link member;
an intermediate link member mounted to a first end portion of said pawl link member and movable in a generally transverse direction relative to said longitudinal axis defined by said frame member in response to pivotal movement of said pawl link member; and
a knife link member received within said leg members of said mounting link member and pivotally mounted in generally the center thereof to said frame member about said second stationary shaft, said knife link member connected to a first end portion of said intermediate link member and pivotally movable in response to transverse movement of said intermediate link member, said knife link member having a cutting edge at a first end thereof.

13. The apparatus according to claim 12, wherein buckle means is provided for securing the strap about the split tissue portions.

14. The apparatus according to claim 13, wherein said buckle means comprises:
a base member including an opening extending therethrough for reception of the first end portion of the strap and having a partial longitudinal channel defined between an upper and lower surface thereof;
clip means pivotally mounted to said upper surface of said base member and movable between an open position to permit reception of the first end portion of the strap and a closed position to securely wedge the strap between a forward edge of said clip means and said base member; and
clamp means slidably housed within said partial longitudinal channel of said base member and movable therewithin from a non-engaging position to an engaging position, said clamp means securely wedging the strap between a forward edge of said clamp means and said base member when in said engaging position.

15. The apparatus according to claim 14, further comprising means for releasably mounting said buckle means.

16. The apparatus according to claim 15, wherein said two separated leg members of said mounting link member are correspondingly dimensioned and configured to receive said buckle means, said leg members each having a partial longitudinal groove at a lower portion thereof, said partial longitudinal grooves correspondingly configured and dimensioned for reception of side portions of said clamp means of said buckle means to releasably mount said buckle means to said mounting link member.

17. The apparatus according to claim 16, wherein said linkage means is actuated by an actuating button, said actuating button slidably mounted on an upper surface of said frame member for reciprocal longitudinal movement between an unadvanced and an advanced position, said actuating button defining a groove on a lower surface thereof to receive an upper portion of said vertical link member; wherein longitudinal movement of said actuating button to said advanced position activates said linkage means to cause pivoting movement of said knife link member and severance of the excess strap, and wherein longitudinal movement of said actuating button to said advanced position also effects pivoting movement. of said mounting link member to cause said leg portions to advance said clamp means to its engaging position against the first end portion of the strap.

18. The apparatus according to claim 17, further comprising spring means for biasing said actuating button to its unadvanced position; wherein release of said actuating button from its advanced position causes said actuating button to return under influence of said spring means to its unadvanced position and said linkage means to its preactuated position, such that said mounting link member assumes its preactuated position with said leg portions releasing said buckle means from its mounting thereto.

19. The apparatus according to claim 16, wherein said advancing means is actuated by a tensioning lever, said tensioning lever being pivotally mounted to said frame member.

20. The apparatus according to claim 19, wherein said linkage means comprises a plurality of interconnected link members, one of said link members being a driving link member, said driving link member adapted for longitudinal advancing movement in response to actuation of said linkage means, said driving link member including a keyway formed therein, said keyway defining first and second apertures connected by a channel.

21. The apparatus according to claim 20, wherein said control means comprises:
   an eccentric shaft rotatably mounted to said frame member and received within said keyway in said driving link member, said eccentric shaft adapted to rotate between a first, a second and a third position, said eccentric shaft having a cross section defining a major axis and a minor axis, said major axis being greater in length than the length of said minor axis;
   at least one locking hook member mounted to said eccentric shaft;
   a locking bar mounted within said tensioning lever and correspondingly positioned to be engaged by said at least one locking hook member; and
   at least one control lever mounted to said eccentric shaft on the exterior of said frame member.

22. The apparatus according to claim 21, wherein said length of said major axis of said eccentric shaft is greater than the width of said channel of said keyway in said driving link member.

23. The apparatus according to claim 22, wherein said length of said minor axis of said eccentric shaft is smaller than the width of said channel of said keyway in said driving link member.

24. The apparatus according to claim 23, wherein said first position of said eccentric shaft corresponds to said first position of said control means wherein said eccentric shaft is received within said first aperture of said driving link member and has its major axis generally transverse to said longitudinal axis defined by said frame member, and wherein said at least one locking hook member engages said locking bar to secure said tensioning lever to said frame member.

25. The apparatus according to claim 24, wherein said second position of said eccentric shaft corresponds to said second position of said control means wherein said at least one locking hook member is released from its engagement with said locking bar to permit pivotal movement of said tensioning lever and tightening of [said]the strap, and wherein said eccentric shaft is received within said first aperture of said driving link member and has its major axis angularly displaced relative to said longitudinal axis defined by said frame member such that said eccentric shaft engages portions of said driving link member defining said channel to prevent longitudinal movement of said driving link member and actuation of said linkage means.

26. The apparatus according to claim 25, wherein said third position of said eccentric shaft corresponds to said third position of said controls means wherein said major axis of said eccentric shaft is generally parallel to said longitudinal axis defined by said frame member such that said eccentric shaft clears said channel of said keyway in said driving link member to permit longitudinal movement of said driving link member relative to said frame member and actuation of said linkage means.

27. The apparatus according to claim 21, wherein said frame member includes at least one recess on an exterior surface thereof, said at least one recess correspondingly configured and dimensioned to receive said at least one control lever.

28. The apparatus according to claim 27, wherein said at least one recess includes first, second and third arcuate-shaped depressions, said arcuate-shaped depressions corresponding to said first, second and third positions of said control means.

29. The apparatus according to claim 28, wherein said at least one control lever includes an arcuate projection correspondingly configured and dimensioned to be received within each of said arcuate-shaped grooves to releasably lock said at least one control lever in each of said three positions of said control means.

30. The apparatus according to claim 10 wherein said manually operable control means includes a control lever selectively moveable relative to said frame member between first, second and third positions.

31. A system for tensioning a strap loop to a predetermined tension about split tissue portions, which comprises:
   frame means adapted to support two end portions of the strap to form a loop about the split tissue portions;
   advancing means for advancing one end portion of the strap loop in a strap tightening direction;
   buckle means for securing the strap loop in the tensioned condition;
   linkage means for severing an excess portion of the strap loop not used in securing the split tissue portions; and
   manually operable control means for controlling operation of said advancing means and said linkage means, said control means being operable independent of said advancing means and said linkage means and being movable between first, second and third positions, said first position corresponding to a secured position of the apparatus, said second position corresponding to an unlocked position to permit actuation of said strap advancing means and said third position corresponding to a release position to permit actuation of said linkage means.

32. The system according to claim 31, wherein said strap advancing means is adapted to release and prevent further tightening of the strap loop when the tension in the strap loop exceeds a predetermined value.

33. The system according to claim 30, wherein said linkage means comprises means for releasably mounting said buckle means.

* * * * *